(12) United States Patent  (10) Patent No.: US 8,702,964 B2
Ahmad  (45) Date of Patent: Apr. 22, 2014

(54) PREPARATION OF MONOBASIC PHOSPHATE IONOPHORES

(75) Inventor: Mohd Rais Ahmad, Kuala Lumpur (MY)

(73) Assignee: Mimos Berhad, Kuala Lumpur (MY)

( * ) Notice: Subject to any disclaimer, the term of this patent is extended or adjusted under 35 U.S.C. 154(b) by 331 days.

(21) Appl. No.: 13/127,298

(22) PCT Filed: Oct. 27, 2009

(86) PCT No.: PCT/MY2009/000175
§ 371 (c)(1),
(2), (4) Date: Oct. 26, 2011

(87) PCT Pub. No.: WO2010/062158
PCT Pub. Date: Jun. 3, 2010

(65) Prior Publication Data
US 2012/0031775 A1  Feb. 9, 2012

(30) Foreign Application Priority Data
Nov. 3, 2008 (MY) .............................. PI20084374

(51) Int. Cl.
*G01N 27/414* (2006.01)

(52) U.S. Cl.
USPC ............. 205/789; 205/782; 204/416; 564/32; 564/47

(58) Field of Classification Search
CPC .............. C07C 275/00–275/70; G01N 27/333; G01N 27/335; G01N 27/414–27/4148
USPC ......... 558/8; 560/335; 562/439, 560; 564/32, 564/33, 38, 44–63; 524/199; 205/782, 789; 204/416–418; 257/253
See application file for complete search history.

(56) References Cited

U.S. PATENT DOCUMENTS 4,649,218 A  3/1987  Shanzer et al.
5,240,573 A  8/1993  Carey
5,380,423 A  1/1995  Reinhoudt et al.

FOREIGN PATENT DOCUMENTS

WO  2009066981  5/2009

OTHER PUBLICATIONS

S. Jeon, et al., "Synthesis and Selective Recognition of Dihydrogen Phosphate by Urea-Anthraquinone" Bull. Korean Chem. Soc., vol. 24, No. 10, 2003, p. 1465-1469.*

Primary Examiner — J. Christopher Ball
(74) Attorney, Agent, or Firm — Bill C. Panagos; Linda D. Kennedy; Butzel Long

(57) ABSTRACT

The present invention relates to the synthesis of lipophilic or immobilized monobasic phosphate ($H_2PO_4$) ionophores (7, 8a, 8b and 11) to be used as ion recognition molecules for monobasic phosphate ($H2PO_4"$) in the cocktail preparation of hydrophobic polymer membranes in ion selective electrode (ISE) or ion-sensitive field effect transistor (ISFET) chemical sensors for detection of monobasic phosphate ($H_2PO_4$) ionic species in soil, synthetic media, hydrophonic liquid, tree sap, ground water and rivers.

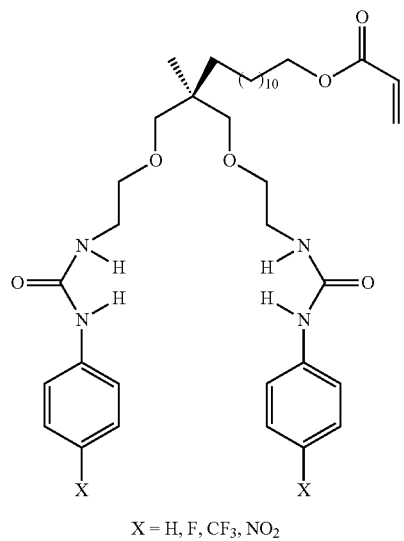

X = H, F, CF$_3$, NO$_2$

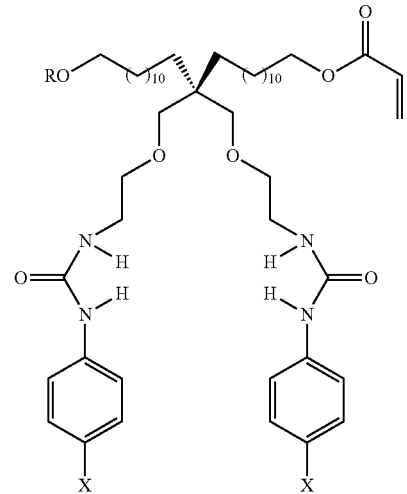

X = H, F, CF$_3$, NO$_2$
8a: R = CH$_3$
8b: R = (CO)CH=CH$_2$

-continued
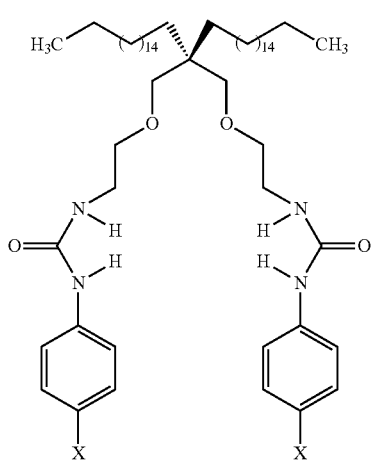
X = H, F, CF$_3$, NO$_2$
19 Claims, No Drawings

PREPARATION OF MONOBASIC PHOSPHATE IONOPHORES

FIELD OF THE INVENTION

The present invention relates to the preparation of anion receptor molecules, more specifically the invention relates to the synthesis of ionophore for monobasic phosphate anion ($H_2PO_4^-$) having high lipophilicity or which can be covalently bonded to backbone of polymeric sensing membrane.

BACKGROUND OF THE INVENTION AND PRIOR ART

Chemical sensor platform has been designed for analysis of the soil macronutrients, namely nitrate ($NO_3^-$), monobasic phosphate ($H_2PO_4^-$), potassium ($K^+$), calcium ($Ca^{2+}$) and, magnesium ($Mg^{2+}$) and for measuring the uptake of these nutrients in plants. The use of the chemical sensor platform can be extended to measurement of ionic contamination in rivers and ground water to detect any excessive use of fertilizers, and ionic poisoning of agriculture products. Environmental pollution as a result of excessive use of nitrate and phosphate has been well documented all over the world. Research results have shown that nitrate poisoning of vegetables such as carrot is detrimental to human early growth.

Existing ion selective electrodes specific for anion typically have poor response characteristics including small linear ranges, high detection limits, and many interferences. Prior attempts to design such anion-specific electrode have been met with considerable difficulty. There is a need for a phosphate ion selective electrode having good selectivity and response characteristics employing existing electrode designs. With the availability of a usable ion selective electrode, non destructive techniques for the measurement of phosphate anions by an ion selective electrode can be applied to all areas of measurement science including environmental, medical and industrial applications.

Polymeric hydrophobic membranes embedded with specific molecules capable of ion recognition (ionophore) give ion selective electrode (ISE) or ion sensitive field effect transistor (ISFET) chemical sensor have the ability to selectively measure the activity and concentration of chemical species.

U.S. Pat. No. 5,380,423 discloses a membrane that is selective for anions, particularly phosphate, comprising an ionophore based on a uranyl complex.

U.S. Pat. No. 6,540,894 B2 discloses a phosphate ion selective electrode, which enables selective measurement of phosphate ion concentration, which is regarded as an important indicator of eutrophication in lakes, marshes, etc. and a method of manufacturing this phosphate ion selective electrode.

U.S. Pat. No. 5,380,423 discloses an anion-selective membrane, in particular a membrane that is selective for the phosphate ion, particularly dihydrogen phosphate. This patent further discloses a sensor in which such an anion-selective membrane is included wherein such sensors are used for measuring the concentration of the anion in an electrolyte solution such as fertilizer dosages in the market gardening sector.

The present invention discloses novel anion ionophores that are lipophilic or which can be covalently bonded to polymeric sensing membrane. More specifically the invention relates to the synthesis of ionophore for monobasic phosphate anion ($H_2PO_4^-$) having high lipophilicity or can be immobilized through cross-linking of the long-chain ($C_{12}$ to $C_{21}$) acrylate moiety with polymer backbone or covalently bonded to backbone of polymeric sensing membrane. The ion recognition molecule is a component in hydrophobic membrane intended for analysis of monobasic phosphate anion ($H_2PO_4^-$) plant nutrient in soil, artificial media, plant sap and hydro phonic liquid, and phosphate pollutant in rivers and ground water.

SUMMARY OF THE INVENTION

The present invention relates to the synthesis of monobasic phosphate ($H_2PO_4^-$) ionophores for detection of monobasic phosphate anionic ($H_2PO_4^-$) species as a component in a sensing membrane. The present invention discloses the synthesis of monobasic phosphate ionophore 7, 8a, 8b and 11.

The monobasic phosphate ionophore 7 is synthesized from diamine 5 wherein diamine 5 is synthesized from silyl ether 2. The synthesis of silyl ether 2 comprising protected diol 1, dilithium tetrachlorocuprate ($Li_2CuCl_4$) and Grignard reagent [$MgBr(CH_2)_nOTBS$] wherein n=9, 10, 11, 12, 13, 14 and 15. The synthesis of diamine 5 comprises de-protected diol silyl ether 2 and 2-bromoethylamine. The synthesis of monobasic phosphate ionophore 7, comprises diamine 5, 4-nitrophenylisocyanate and acryloyl chloride.

The structures of monobasic phosphate ionophore 7, diamine 5 and silyl ether 2 are as below:

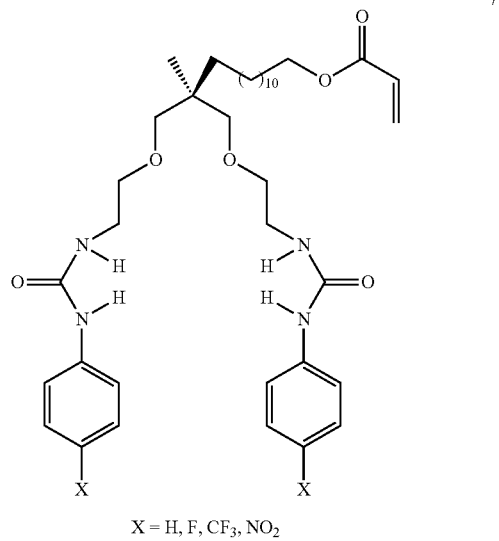

X = H, F, $CF_3$, $NO_2$

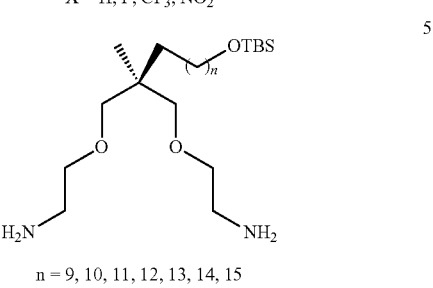

n = 9, 10, 11, 12, 13, 14, 15

-continued

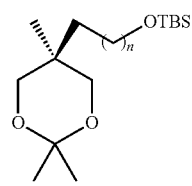

n = 9, 10, 11, 12, 13, 14, 15

-continued

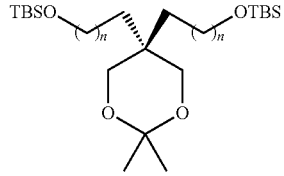

n = 9, 10, 11, 12, 13, 14, 15

The monobasic phosphate ionophore 11 is synthesized from diamine 10 wherein diamine 10 is synthesized from silyl ether 9. The synthesis of silyl ether 9 comprises ditosylate protected diol 3, dilithium tetrachlorocuprate ($Li_2CuCl_4$) and Grignard reagent [$MgBr(CH_2)_nOTBS$] wherein n=15, 16, 17, 18 and 19. The synthesis of diamine 10 comprises de-protected diol 9 and 2-bromoethylamine. The synthesis of monobasic phosphate ionophore 11 comprises diamine 10, 4-nitrophenylisocyanate and acryloyl chloride.

The monobasic phosphate ionophore 8a or 8b is synthesized from diamine 6 wherein diamine 6 is synthesized from silyl ether 4. The synthesis of silyl ether 4 comprises ditosylate protected diol 3, dilithium tetrachlorocuprate ($Li_2CuCl_4$) and Grignard reagent [$MgBr(CH_2)_nOTBS$] wherein n=9, 10, 11, 12, 13, 14 and 15. The synthesis of diamine 6 comprising de-protected diol silyl ether 4 and 2-bromoethylamine. The synthesis of monobasic phosphate ionophore 8a or 8b comprises diamine 6, 4-nitrophenylisocyanate and acryloyl chloride.

The structures of monobasic phosphate ionophore 8a or 8b, diamine 6 and silyl ether 4 are as below:

The structures of monobasic phosphate ionophore 11, diamine 10 and silyl ether 9 are as below:

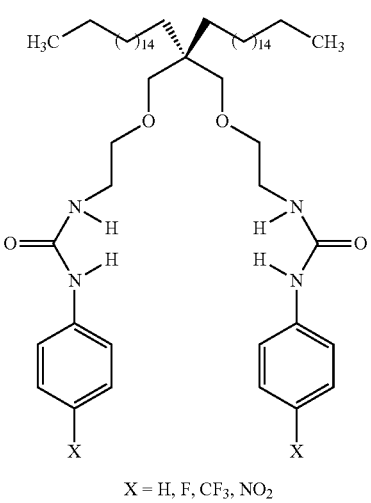

X = H, F, $CF_3$, $NO_2$

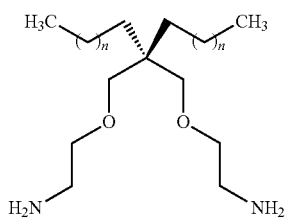

n = 15, 16, 17

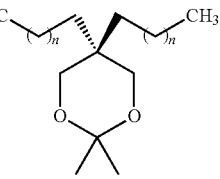

n = 15, 16, 17, 18, 19

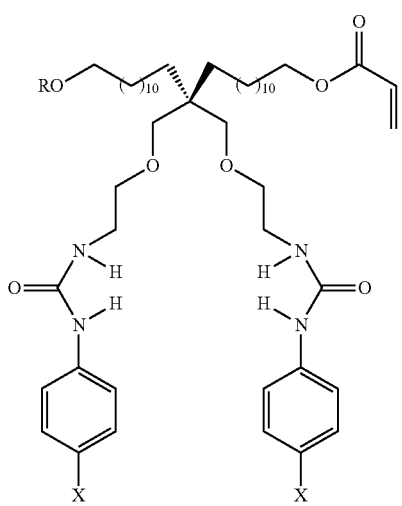

X = H, F, $CF_3$, $NO_2$
8a: R = $CH_3$
8b: R = (CO)CH=$CH_2$

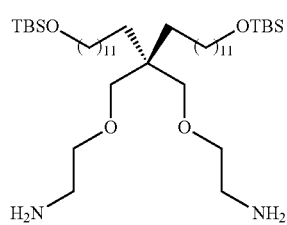

n = 9, 10, 11, 12, 13, 14, 15

In this invention, 4-nitrophenylisocyanate reagent is used and further more the para nitro substituent in the phenylisocyanate reagent can be replaced with H, F, $CF_3$, Cl and $SO_3R$ at the same para position to give similar results.

The monobasic phosphate ($H_2PO_4^-$) ionophores are used for detecting soil macronutrient, plant nutrient uptake, phosphate contaminant in ground water, phosphate contaminant in rivers and phosphate poison in agriculture products such as vegetables wherein the nutrient and contaminant ionic species are detected by means of a chemical sensor in combination with the monobasic phosphate ($H_2PO_4^-$) ionophore. The chemical sensor being used is ion sensitive field effect transistor (ISFET) sensor cell and ion selective electrode (ISE) sensor cell.

DETAILED DESCRIPTION OF THE INVENTION

The present invention relates to the synthesis of lipophilic or immobilized ionophore for analysis of monobasic phosphate ($H_2PO_4^-$) ionic species in soil, synthetic media, hydrophonic liquid, tree sap, ground water and rivers based on ion sensitive field effect transistor (ISFET) or ion selective electrode (ISE) chemical sensor devices.

The present invention discloses the economical routes for preparation of lipophilic or immobilized monobasic phosphate ($H_2PO_4^-$) ionophores for large volume manufacturing purposes. All ion recognition neutral molecules can be prepared using readily available starting materials, reagents and conditions as described later.

The preparation of the target molecules uses starting materials that can be procured economically at large quantities and high purity. Pentaerythritol (2,2-bis(hydroxymethyl)1,3-propanediol) (i) and 2,2-bis(hydroxymethyl)propionic acid (ii), readily available from commercial sources and at low cost, are the starting materials for monobasic phosphate ($H_2PO_4^-$) ionophore. Two hydroxyl groups (1,3-diol) in i and ii are protected in a cyclic ketal form that is resistant to nucleophilic attack and can be de-protected in acidic condition. In its ketal form the remaining two hydroxyl groups in i can be converted to good leaving groups such as tosylate (OTs) or bromide (Br). In its protected form, the carboxylic group in ii can be reduced by hydride to hydroxymethyl moiety that can be converted further to tosylate or bromide leaving groups.

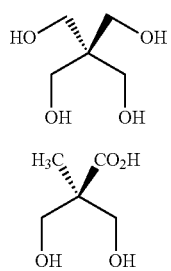

i ii

Derivatives of i and ii can be transformed to monobasic phosphate ($H_2PO_4^-$) ionophores if it is converted to lipophilic molecule exhibiting selective binding to the target anion. Hydrogen bonding is a good mechanism of binding between a large neutral molecule and anion. Deprotected diols 2, 4 and 9 can be converted into the respective diamines 5, 6 and 10, by reacting with 2-bromoethylamine.

The resulting diamines can be reacted with phenylisocyanate or its derivatives to give lipophilic or immobilized bisurea lariats that bind selectively to monobasic phosphate ($H_2PO_4^-$) anion via hydrogen bonding interaction. Upon desilylation of 5 or 6 the de-protected hydroxyl group or diol can be acrylated with acryloyl chloride in anhydrous pyridine to give ionophores 7, 8a, 8b and 11. Upon polymerization with acrylic monomer or oligomer the ionophore is covalently bonded to the polymer backbone and is therefore immobilized to the sensing membrane. Electron-withdrawing group such as fluoride (F), trifluoromethyl ($CF_3$) or nitro ($NO_2$) can substitute the para hydrogen (H) in phenylisocyanate to improve the performance of the ionophores. In this invention, 4-nitrophenylisocyanate reagent is used and further more the para nitro substituent in the phenylisocyanate reagent can be replaced with H, F, $CF_3$, Cl and $SO_3R$ at the same para position to give similar results. The synthesized ionophore is a phosphate recognition component in sensing membrane cocktail for analysis of monobasic phosphate ($H_2PO_4^-$) anionic plant macronutrient in soil, synthetic media, hydro phonic liquid, and plant sap, and phosphate pollutant in rivers and ground water.

The prepared cocktails can be applied on ion selective electrode (ISE) or ion sensitive field effect transistor (ISFET) surface and the sensitivity and selectivity of the hydrophobic membrane can be characterized from response and selectivity plots.

Example 1

Synthesis of Protected Diol Silyl Ether 2

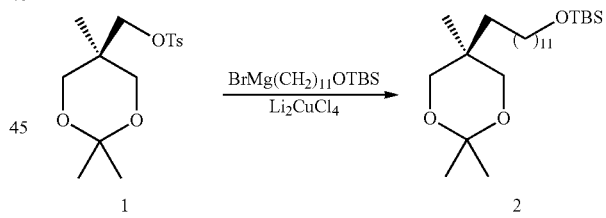

An apparatus consisting of a round-bottomed 100 ml three-necked flask equipped with addition funnel, thermometer, magnetic stir bar and a syringe inlet was set up and flushed with a blanket of argon gas. Dilithium tetrachlorocuprate ($Li_2CuCl_4$), 0.5 mmol in 10 mL tetrahydrofuran (THF), was prepared by mixing $CuCl_2$ (0.142 g) and LiCl (0.071 g). Then, protected diol tosylate 1 (25 mmol) in 25 mL THF was added. Grignard reagent [$MgBr(CH_2)_{11}OTBS$] was added dropwise over 30 minutes at −30° C. with stirring. Stirring was continued for an additional hour, before the reaction mixture was allowed to warm to room temperature and stirring was continued for additional 10 hours. The reaction mixture was quenched with dilute hydrochloric acid and diluted with 200 mL of distilled water and extracted three times with 50 mL portions of diethyl ether. The combined organic layers were washed with brine and dried successively with anhydrous sodium sulfate and magnesium sulfate and vacuum evaporated. The residue was eluted through silica-gel column with hexane-ethyl acetate to give 83% yield of protected diol silyl ether 2.

Example 2

Synthesis of Silyl Ether Diamine 5

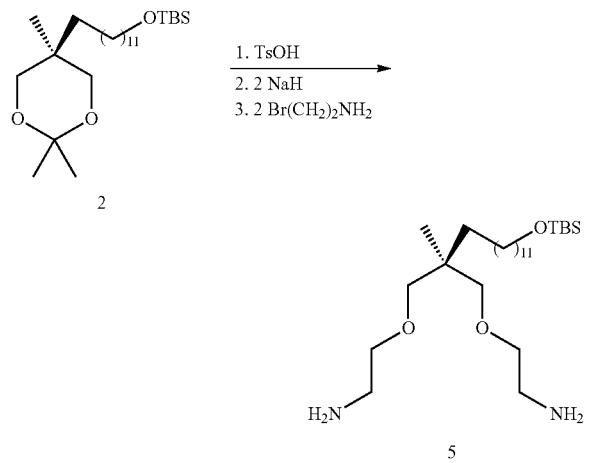

To a 250-mL three-necked, round-bottomed flask equipped with a reflux condenser, addition funnel, magnetic stir bar and a syringe inlet was placed 50 mL of freshly distilled THF. The system was flushed with a steady flow of argon and sodium hydride (0.63 g, 26.25 mmol) was added into the flask. The flask is chilled with ice-water bath and 6.55 mmol of de-protected diol silyl ether 2 was added dropwise into the flask. The reaction mixture is stirred for additional 1 hr. 2-Bromo-ethyl amine (7.0 mmol) in 50 mL of THF was added over 20 minutes. The reaction mixture is stirred for 1 hr before the bath is removed and the reaction mixture was stirred at room temperature for additional 12 hr and quenched with dropwise of water. The THF solvent was removed by distillation. Methylene chloride (100 mL) and 50 mL of 10% HCl were added to the residue. The organic layer was washed with water, dried over magnesium sulfate and the solvent distilled off. Crystallization from methanol gives 92% of silyl ether diamine 5.

Example 3

Synthesis of Monobasic Phosphate Ionophore 7

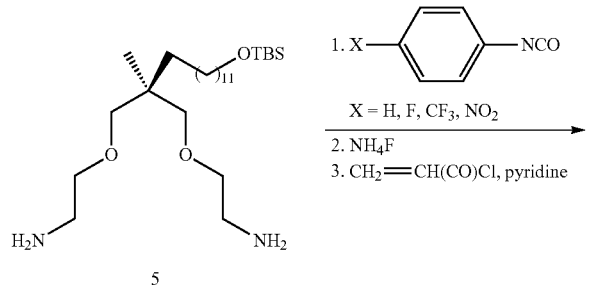

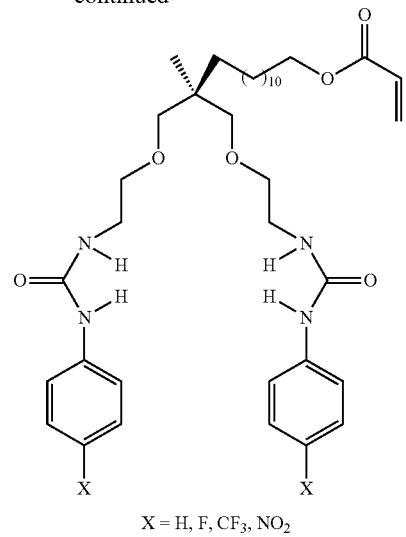

X = H, F, CF$_3$, NO$_2$

7

An oven-dried 250-mL three-necked, round-bottomed flask equipped with a reflux condenser, addition funnel, magnetic stir bar was kept under steady flow of argon. A solution of 0.02 mol of silyl ether diamine 5 in 40 mL THF was added to a stirred solution of 4-nitrophenylisocyanate (0.030 mol) in 100 mL THF. After stirring for at room temperature for 12 hr, the precipitate formed was filtered under vacuum suction and washed twice with 50 mL portions of THF. Recrystallization from THF gives yellow crystals. Deprotection of silyl ether was done with tetrabutyl ammonium fluoride. The de-protected hydroxyl is acrylated with acryloyl chloride in pyridine to gives 81% of monobasic phosphate ionophore 7 (x=NO$_2$).

Example 4

Synthesis of Protected Diol DiSilyl Ether 4

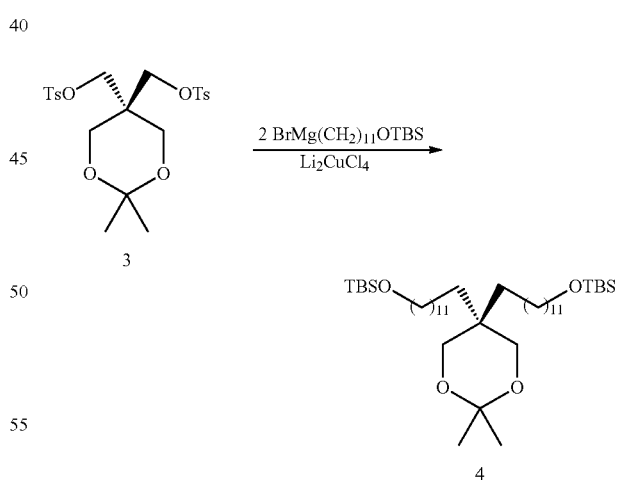

An apparatus consisting of a round-bottomed 100 ml three-necked flask equipped with addition funnel, thermometer, magnetic stir bar and a syringe inlet was set up and flushed with blanket of argon gas. Dilithium tetrachlorocuprate (Li$_2$CuCl$_4$), 0.5 mmol in 10 mL THF, was prepared by mixing CuCl$_2$ (0.142 g) and LiCl (0.071 g). Then, protected diol ditosylate 3 (25 mmol) in 25 mL THF was added. Grignard reagent [MgBr(CH$_2$)$_{11}$OTBS], 50 mmol in 25 mL THF was added drop-wise over 30 min at −30° C. with stirring. Stirring was continued for additional 1 hr, before the reaction mixture was allowed to warm to room temperature and stirring was continued for an additional 10 hrs. The reaction mixture was quenched with dilute HCl and diluted with 200 mL of distilled water and extracted three times with 50 mL portions of diethyl ether. The combined organic layers were washed with brine and dried successively with sodium sulfate and magnesium sulfate and vacuum evaporated. The residue was eluted through silica-gel column with hexane-ethyl acetate to give 78% yield of protected diol disilyl ether 4.

Example 5

Synthesis of Disilyl Ether Diamine 6

To a 250-mL three-necked, round-bottomed flask equipped with a reflux condenser, addition funnel, magnetic stir bar and a syringe inlet was placed 50 mL of dry THF. The system was flushed with a steady flow of argon and sodium hydride (0.63 g, 26.25 mmol) was added into the flask. The flask is chilled with ice-water bath and 6.55 mmol of de-protected diol disilylether 4 was added dropwise into the flask. The reaction mixture is stirred for additional 1 hr. 2-Bromoethylamine (7.0 mmol) in 50 mL of THF was added over 20 minutes. The reaction mixture is stirred for 1 hr before the bath is removed and the reaction mixture was stirred at room temperature for additional 12 hr and quenched with drop-wise of water. The THF solvent was removed by distillation. Methylene chloride (100 mL) and 50 mL of 10% HCl were added to the residue. The organic layer was washed with water, dried over magnesium sulfate and the solvent distilled off. Crystallization from methanol gives 78% of disilyl ether diamine 6.

Example 6

Synthesis of Monobasic Phosphate Ionophores 8a and 8b

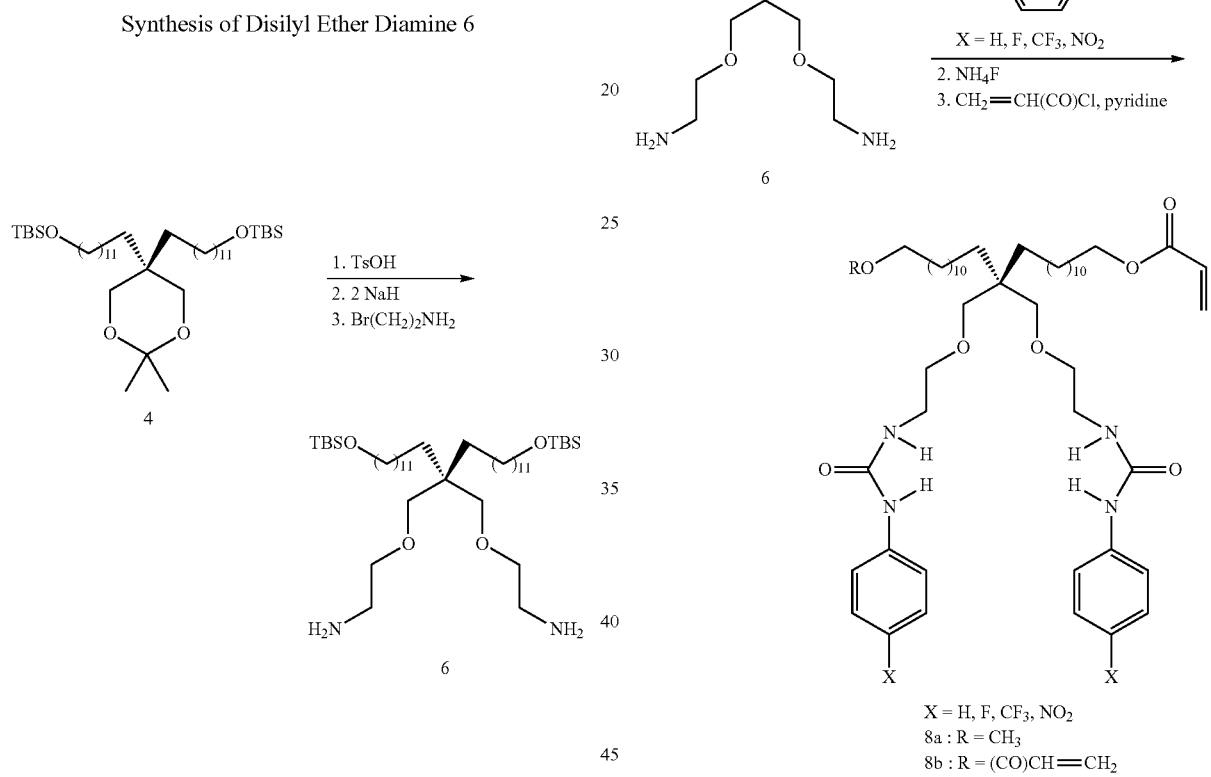

An oven-dried 250-mL three-necked, round-bottomed flask equipped with a reflux condenser, addition funnel, magnetic stir bar was kept under steady flow of argon. A solution of 0.02 mol of disilyl ether diamine 6 in 40 mL THF was added to a stirred solution of 4-nitrophenylisocyanate (0.030 mol) in 100 mL THF. After stirring for at room temperature for 12 hr, the precipitate formed was filtered under vacuum suction and washed twice with 50 mL portions of THF. Recrystallization from THF gives yellow crystals.

Deprotection of silyl ether was done with tetrabutyl ammonium fluoride. The de-protected hydroxyl groups are acrylated with acryloyl chloride in pyridine to gives 85% of monobasic phosphate ionophore 8b (x=$NO_2$).

Example 7

Synthesis of Lipophilic Protected Diol 9

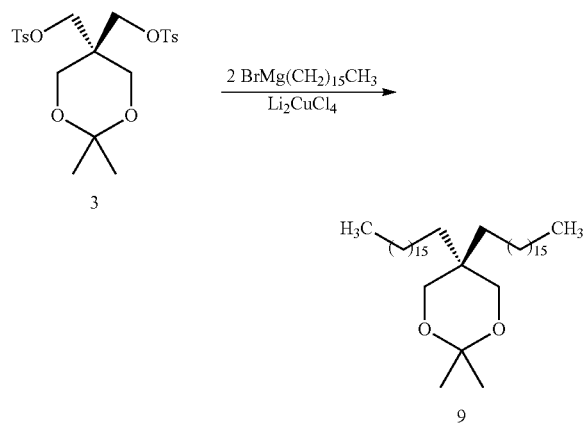

An apparatus consisting of a round-bottomed 100 mL three-necked flask equipped with addition funnel, thermometer, magnetic stir bar and a syringe inlet was set up and flushed with blanket of argon gas. Dilithium tetrachlorocuprate ($Li_2CuCl_4$), 0.5 mmol in 10 mL THF, was prepared by mixing $CuCl_2$ (0.142 g) and LiCl (0.071 g). Then, protected diol ditosylate 3 (25 mmol) in 25 mL THF was added. Dodecylmagnesiumbromide Grignard reagent [$MgBr(CH_2)_{11}CH_3$], 50 mmol in 25 mL THF was added drop-wise over 30 min at −30° C. with stirring. Stirring was continued for additional 1 hr, before the reaction mixture was allowed to warm to room temperature and stirring was continued for additional 10 hr. The reaction mixture was quenched with dilute HCl and diluted with 200 mL of distilled water and extracted three times with 50 mL portions of diethyl ether. The combined organic layers were washed with brine and dried successively with sodium sulfate and magnesium sulfate and vacuum evaporated. The residue was eluted through silica-gel column with hexane-ethyl acetate to give 76% yield of protected diol 9.

Example 8

Synthesis of Lipophilic Diamine 10

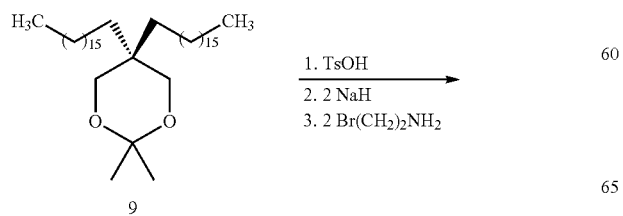

-continued

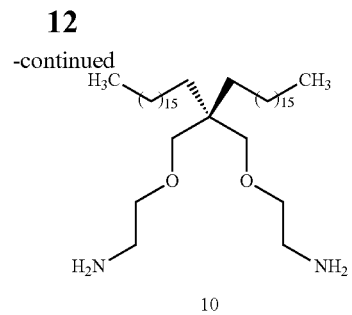

To a 250-mL three-necked, round-bottomed flask equipped with a reflux condenser, addition funnel, magnetic stir bar and a syringe inlet was placed 50 mL of dry THF. The system was flushed with a steady flow of argon and sodium hydride (0.63 g, 26.25 mmol) was added into the flask. The flask is chilled in an ice-water bath and 6.55 mmol of de-protected lipophilic diol 9 was added dropwise into the flask. The reaction mixture is stirred for an additional 1 hr. 2-Bromoethylamine (7.0 mmol) in 50 mL of THF was added over 20 minutes. The reaction mixture is stirred for about 1 hr before the bath is removed and the reaction mixture was stirred at room temperature for additional 12 hr and quenched with drop-wise of water. The THF solvent was removed by distillation. Methylene chloride (100 mL) and 50 mL of 10% HCl were added to the residue. The organic layer was washed with water, dried over magnesium sulfate and the solvent distilled off. Crystallization from methanol gives 81% of lipophilic diamine 10.

Example 9

Synthesis of Monobasic Phosphate Ionophore 11

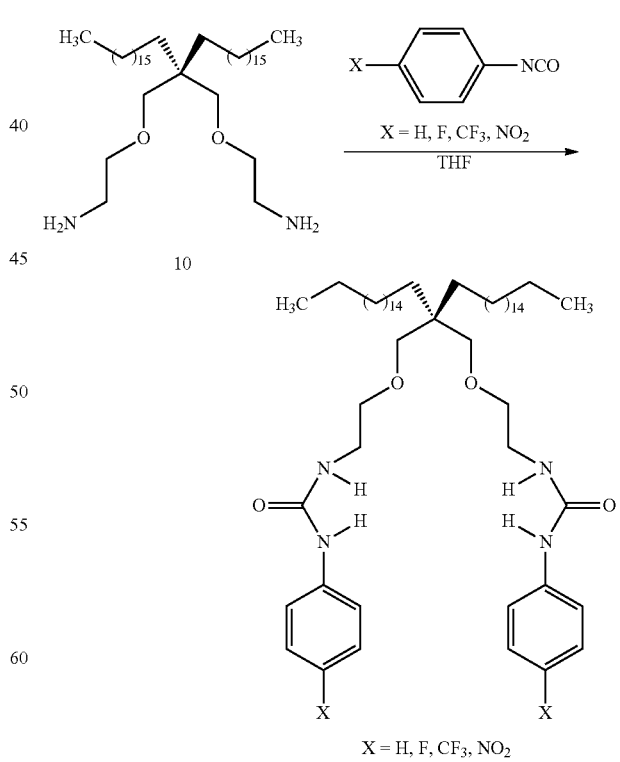

An oven-dried 250-mL three-necked, round-bottomed flask equipped with a reflux condenser, addition funnel, magnetic stir bar was kept under steady flow of argon. A solution of 0.02 mol of diamine 10 in 40 mL THF was added to a stirred solution of 4-nitrophenylisocyanate (0.030 mol) in 100 mL THF. After stirring for at room temperature for 12 hr, the precipitate formed was filtered under vacuum suction and washed twice with 50 mL portions of THF. Recrystallization from THF gives yellow crystals. Deprotection of silyl ether was done with tetrabutyl ammonium fluoride. The de-protected hydroxyl groups are acrylated with acryloyl chloride in pyridine to gives 81% of monobasic phosphate ionophore 11 (x=$NO_2$).

The invention claimed is:

1. A method of detecting soil macronutrient, plant nutrient uptake, phosphate contaminant in ground water, phosphate contaminant in rivers and phosphate poison in agriculture products, comprising:

introducing a monobasic phosphate ($H_2PO_4$—) ionophore synthesized using diamine synthesized using silyl ether to a sample of soil, plant, ground water, river water or agricultural product to detect nutrient and contaminant ionic species.

2. The method of claim 1 further comprising introducing a chemical sensor in combination with the monobasic phosphate ($H_2PO_4$—) ionophore.

3. The method of claim 2 wherein the chemical sensor comprises an ion sensitive field effect transistor (ISFET) sensor cell.

4. The method of claim 2 wherein the chemical sensor comprises an ion selective electrode (ISE) sensor cell.

5. A method of preparing monobasic phosphate ($H_2PO_4$—) ionophore comprising synthesis of monobasic phosphate ionophore from diamine wherein diamine is synthesized from silyl ether.

6. The method of preparing monobasic phosphate ($H_2PO_4$—) ionophore according to claim 5 wherein the synthesis of silyl ether comprises protected diol, dilithium tetrachlorocuprate ($Li_2CuCl_4$) and Grignard reagent [MgBr $(CH_2)_n$OTBS] wherein n=9, 10, 11, 12, 13, 14 and 15.

7. The method of preparing monobasic phosphate ($H_2PO_4$—) ionophore according to claim 5 wherein said silyl ether has the formula:

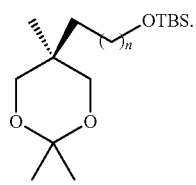

n = 9, 10, 11, 12, 13, 14, 15

8. The method of preparing monobasic phosphate ($H_2PO_4$—) ionophore according to claim 5 wherein the synthesis of diamine comprises deprotected diol silyl ether and 2-bromoethylamine.

9. The method of preparing monobasic phosphate ($H_2PO_4$—) ionophore according to claim 5 wherein said diamine has the formula:

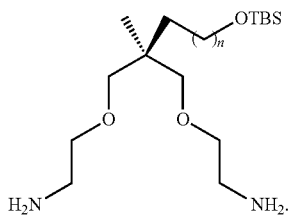

n = 9, 10, 11, 12, 13, 14, 15

10. The method of preparing monobasic phosphate ($H_2PO_4$—) ionophore according to claim 5 wherein the synthesis of monobasic phosphate ionophore comprises diamine, 4-nitrophenylisocyanate and acryloyl chloride.

11. The method of preparing monobasic phosphate ($H_2PO_4$—) ionophore according to claim 5 wherein said monobasic phosphate ionophore has the formula:

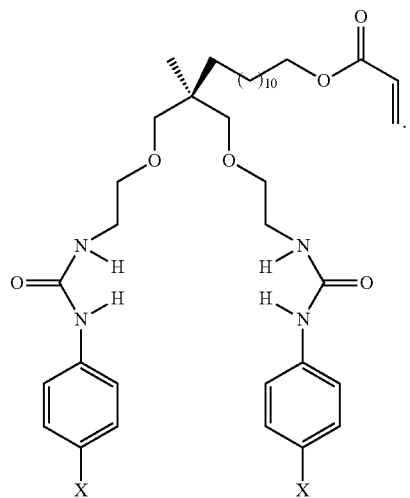

X = H, F, $CF_3$, $NO_2$

12. The method of preparing monobasic phosphate ($H_2PO_4$—) ionophore according to claim 5 wherein said silyl ether has the formula:

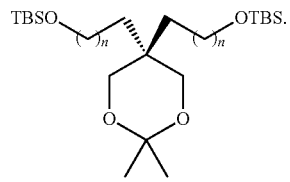

n = 9, 10, 11, 12, 13, 14, 15

13. The method of preparing monobasic phosphate ($H_2PO_4$—) ionophore according to claim 5 wherein said diamine has the formula:

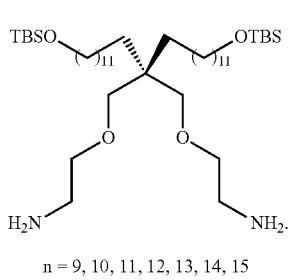

n = 9, 10, 11, 12, 13, 14, 15

14. The method of preparing monobasic phosphate ($H_2PO_4-$) ionophore according to claim 5 wherein said ionophore has the formula:

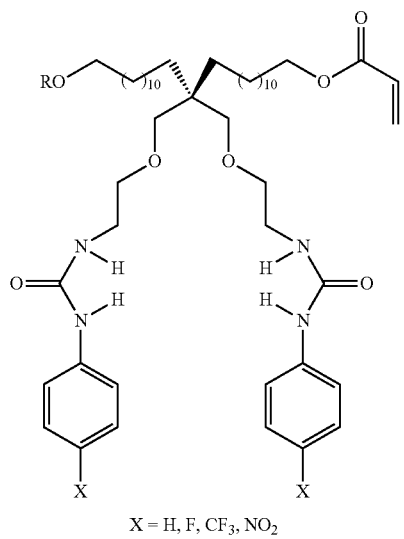

X = H, F, $CF_3$, $NO_2$ wherein R is $CH_3$ or (CO)CH=$CH_2$.

15. The method of preparing monobasic phosphate ($H_2PO_4-$) ionophore according to claim 5 wherein the synthesis of silyl ether comprises ditosylate protected diol, dilithium tetrachlorocuprate ($Li_2CuCl_4$) and Grignard reagent [MgBr($CH_2$)$_n$OTBS] wherein n=15, 16, 17, 18 and 19.

16. The method of preparing monobasic phosphate ($H_2PO_4-$) ionophore according to claim 5 wherein said silyl ether has the formula:

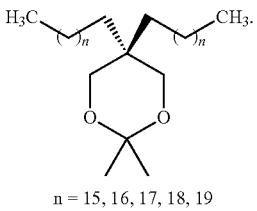

n = 15, 16, 17, 18, 19

17. The method of preparing monobasic phosphate ($H_2PO_4-$) ionophore according to claim 5 wherein said diamine has the formula:

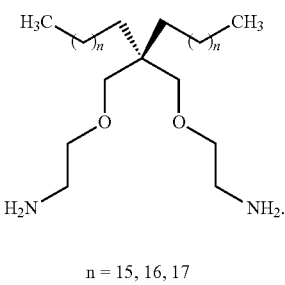

n = 15, 16, 17

18. The method of preparing monobasic phosphate ($H_2PO_4-$) ionophore according to claim 5 wherein said monobasic phosphate ($H_2PO_4-$) ionophore has the formula:

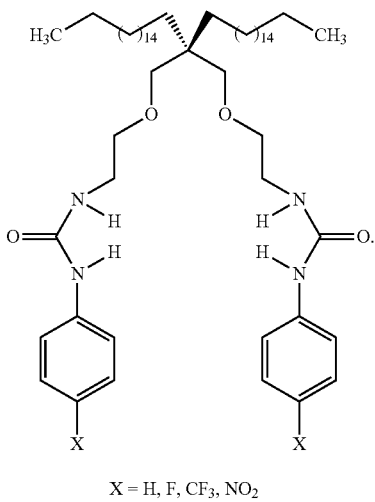

X = H, F, $CF_3$, $NO_2$

19. The 4-nitrophenylisocyanate reagent according to claim 10 wherein the para nitro substituent in the phenylisocyanate reagent is replaced with H, F, $CF_3$, Cl and $SO_3R$ at the same para position.

* * * * *